(12) United States Patent
Datta et al.

(10) Patent No.: US 12,731,314 B2
(45) Date of Patent: Sep. 8, 2026

(54) SYSTEM AND METHOD FOR AN INTELLIGENT SCOUT SCAN TECHNIQUE TO IDENTIFY A HIGH CONTRAST OBJECT IN A COMPUTED TOMOGRAPHY SCANNER

(71) Applicant: GE Precision Healthcare LLC, Wauwatosa, WI (US)

(72) Inventors: Arka Datta, Pewaukee, WI (US); John Moore Boudry, Waukesha, WI (US); Roy-Arnulf Helge Nilsen, Waukesha, WI (US); Brian Edward Nett, Wauwatosa, WI (US); Holly Ann McDaniel, Waukesha, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 736 days.

(21) Appl. No.: 18/106,614

(22) Filed: Feb. 7, 2023

(65) Prior Publication Data

US 2024/0265590 A1 Aug. 8, 2024

(51) Int. Cl.

*G06T 12/10* (2026.01)
*A61B 6/00* (2024.01)
*A61B 6/03* (2006.01)

(52) U.S. Cl.

CPC .............. *G06T 12/10* (2026.01); *A61B 6/032* (2013.01); *A61B 6/52* (2013.01)

(58) Field of Classification Search

CPC ............ G06T 11/005; G06T 7/11; A61B 6/12
See application file for complete search history.

(56) References Cited

U.S. PATENT DOCUMENTS

| | | | | |
|---|---|---|---|---|
| 8,891,847 | B2 * | 11/2014 | Helm | G06T 11/00 382/131 |
| 9,074,986 | B2 * | 7/2015 | Pal | A61B 6/545 |
| 9,684,961 | B2 | 6/2017 | Senegas et al. | |
| 10,706,550 | B2 * | 7/2020 | Sun | A61B 6/037 |
| 2009/0010505 | A1 | 1/2009 | Cocosco et al. | |
| 2018/0049715 | A1 * | 2/2018 | Zebaze | A61B 6/032 |
| 2021/0137634 | A1 * | 5/2021 | Lang | A61B 5/113 |
| 2022/0031273 | A1 * | 2/2022 | Lewis | A61B 6/527 |
| 2022/0036609 | A1 * | 2/2022 | Vuppala | A61B 6/032 |
| 2022/0071578 | A1 * | 3/2022 | Schildkraut | A61B 6/032 |
| 2022/0207722 | A1 * | 6/2022 | Kim | G06T 7/0012 |
| 2023/0038493 | A1 * | 2/2023 | Villongco | A61B 8/483 |
| 2023/0230230 | A1 * | 7/2023 | Gong | G06T 7/0012 600/300 |
| 2025/0061568 | A1 * | 2/2025 | Flaeschner | A61B 6/466 |

FOREIGN PATENT DOCUMENTS

| | | |
|---|---|---|
| JP | 4083675 | 4/2008 |
| JP | 4509497 | 7/2010 |
| JP | 4542259 | 9/2010 |
| JP | 2012040284 | 3/2012 |

* cited by examiner

*Primary Examiner* — Benjamin O Dulaney
(74) *Attorney, Agent, or Firm* — Fletcher Yoder, P.C.

(57) ABSTRACT

A computer-implemented method includes generating an image from scan data acquired during a non-diagnostic scan utilizing a computed tomography scanner. The computer-implemented method also includes performing object segmentation based on pixel connectivity on the image to generate segmented regions. The computer-implemented method further includes characterizing pixel connectivity properties of the segmented regions. The computer-implemented method still further includes obtaining respective bounding shape coordinates and area for bounding shapes of the segmented regions.

6 Claims, 11 Drawing Sheets

SYSTEM AND METHOD FOR AN INTELLIGENT SCOUT SCAN TECHNIQUE TO IDENTIFY A HIGH CONTRAST OBJECT IN A COMPUTED TOMOGRAPHY SCANNER

BACKGROUND

The subject matter disclosed herein relates to medical imaging systems and, more particularly, to a system and a method for an intelligent scout scan technique to identify a high contrast object in a computed tomography (CT) scanner.

In computed tomography (CT), X-ray radiation spans an object or a subject of interest being scanned, such as a human patient, baggage, or other object, and a portion of the radiation impacts a detector where the image data is collected. In digital X-ray systems a photodetector produces signals representative of the amount or intensity of radiation impacting discrete pixel regions of a detector surface. The signals may then be processed to generate an image that may be displayed for review. In the images produced by such systems, it may be possible to identify and examine the internal structures and organs within a subject's body. In CT imaging systems a detector array, including a series of detector elements or sensors, produces similar signals through various positions as a gantry is displaced around a subject or object being imaged, allowing volumetric image reconstructions to be obtained.

During CT imaging, a high contrast object or a high attenuating object such as metal or contrast drop (or contrast spill) can create a significant artifact in the reconstructed image. It is recommended to follow some precaution (e.g., clean the contrast drop) during a patient preparation step to keep such an artifact from occurring. However, these procedures are difficult to follow for a busy medical center (especially since a small contrast drop is difficult to identify). A scout scan is an integral part of a pre-scan workflow which is performed prior to the actual CT scan (e.g., diagnostic scan) to set appropriate landmarks containing the region of interest of the patient. Current scout scan techniques do not include any process for detecting a high contrast object in a scout scan.

SUMMARY

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In one embodiment, a computer-implemented method for identifying a high contrast or highly attenuating object in medical imaging data is provided. The computer-implemented method includes generating, via a processor, an image from scan data acquired during a non-diagnostic scan utilizing a computed tomography (CT) scanner. The computer-implemented method also includes performing, via the processor, object segmentation based on pixel connectivity on the image to generate segmented regions. The computer-implemented method further includes characterizing, via the processor, pixel connectivity properties of the segmented regions. The computer-implemented method still further includes obtaining, via the processor, respective bounding shape coordinates and area for bounding shapes of the segmented regions. The computer-implemented method even further includes designating, via the processor, a first bounding shape of the bounding shapes as a subject bounding shape for a subject scanned during the non-diagnostic scan.

In another embodiment, a computer-implemented method for identifying a high contrast or highly attenuating object in medical imaging data is provided. The computer-implemented method includes generating, via a processor, a scout image from scan data acquired during a scout scan of a subject utilizing a computed tomography (CT) scanner. The computer-implemented method also includes determining, via the processor, whether a high contrast or highly attenuating object is detected within the scout scan. The computer-implemented method further includes proceeding, via the processor, with a scanning session when no high contrast or highly attenuating object is detected. The computer-implemented method even further includes determining, via the processor, whether the high contrast or highly attenuating object is outside a body of the subject when the high contrast or highly attenuating object is detected. The computer-implemented method yet further includes causing, via the processor, display of a composite image of the scout image with a location of the high contrast or highly attenuating object overlaid on the scout image on a display when the high contrast or highly attenuating object is outside body.

In a further embodiment, a computer-implemented method for identifying a high contrast or highly attenuating object on a component of a computed tomography (CT) scanner. The computer-implemented method includes generating, via a processor, a first plurality of images from scan data acquired during an air scan utilizing the CT scanner, where during the air scan a table of the CT scanner is not disposed within a bore of a gantry of the CT scanner. The computer-implemented method also includes determining, via the processor, whether a high contrast or highly attenuating object is detected within at least one image of the first plurality of images. The computer-implemented method further includes causing, via the processor, display of a first alert of contamination on a scan window of the CT scanner on a display when the high contrast or highly attenuating object is detected within at least one image of the first plurality of images.

BRIEF DESCRIPTION OF THE DRAWINGS

These and other features, aspects, and advantages of the present disclosed subject matter will become better understood when the following detailed description is read with reference to the accompanying drawings in which like characters represent like parts throughout the drawings, wherein.

DETAILED DESCRIPTION

Figure 1:
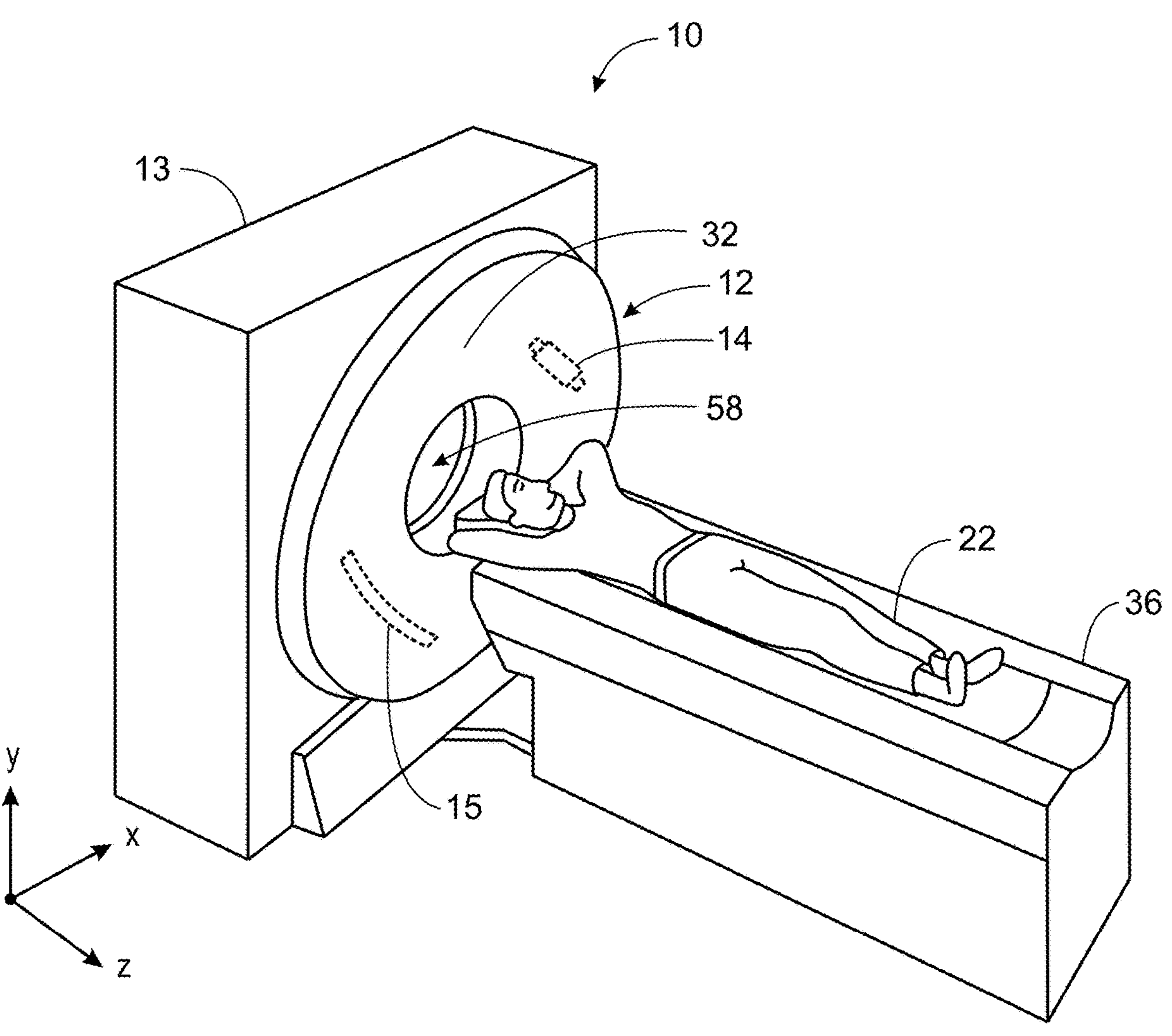
FIG. 1 is a pictorial representation of a CT imaging system, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion may be provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as tomographic image reconstruction for industrial Computed Tomography (CT) used in non-destructive inspection of manufactured parts or goods (i.e., quality control or quality review applications), and/or the non-invasive inspection of packages, boxes, luggage, and so forth (i.e., security or screening applications). In general, the present approaches may be useful in any imaging or screening context to provide reconstructed images without artifacts due to contrast drop or spill.

The present disclosure provides systems and methods for an intelligent scout scan (or calibration scan) technique to identify high contrast object (or high attenuating object) in a computed tomography (CT) scanner. In particular, the disclosed techniques obtain scan data (e.g., scout scan data, air scan data, calibration scan data) from the pre-scan workflow (i.e., before a diagnostic scan) and the scan data are processed to generate images (e.g., binary images such as grayscale images). Individual objects are detected (and segmented) and characterized based on pixel connectivity properties. The characterization may include area, centroid, orientation, circularity, eccentricity, and so forth. These segmented regions or objects are processes with a dynamic table to determine overlapping and non-overlapping identified regions. The unique (non-overlapping) region parameters are saved and highlighted as an overlay image on a displayed composite image indicating the high contrast object. Alerts and/or recommendations (e.g., to clean the contrast spill) may be provided to the operator related to the detected high contrast object. The disclosed techniques provide a process to detect a high contrast object during a scout scan. In addition, the disclosed techniques can be integrated within any existing scan data such as air scans during fast calibration to improve robustness of the scan window check during detailed or daily calibration. Further, the disclosed techniques can be utilized as a standalone feature. The disclosed techniques provide a safety check feature to ensure CT data acquisition is free from any unintended high attenuating object in the scan field of view (SFOV) and improve clinical workflow robustness. In addition, the disclosed techniques provide a holistic approach combining system hardware along with software for computation and analysis to improve the efficiency and robustness of the workflow by detecting and identifying high attenuation objects that may produce artifacts in the reconstructed images and alerting an operator to follow appropriate procedures.

Figure 2:
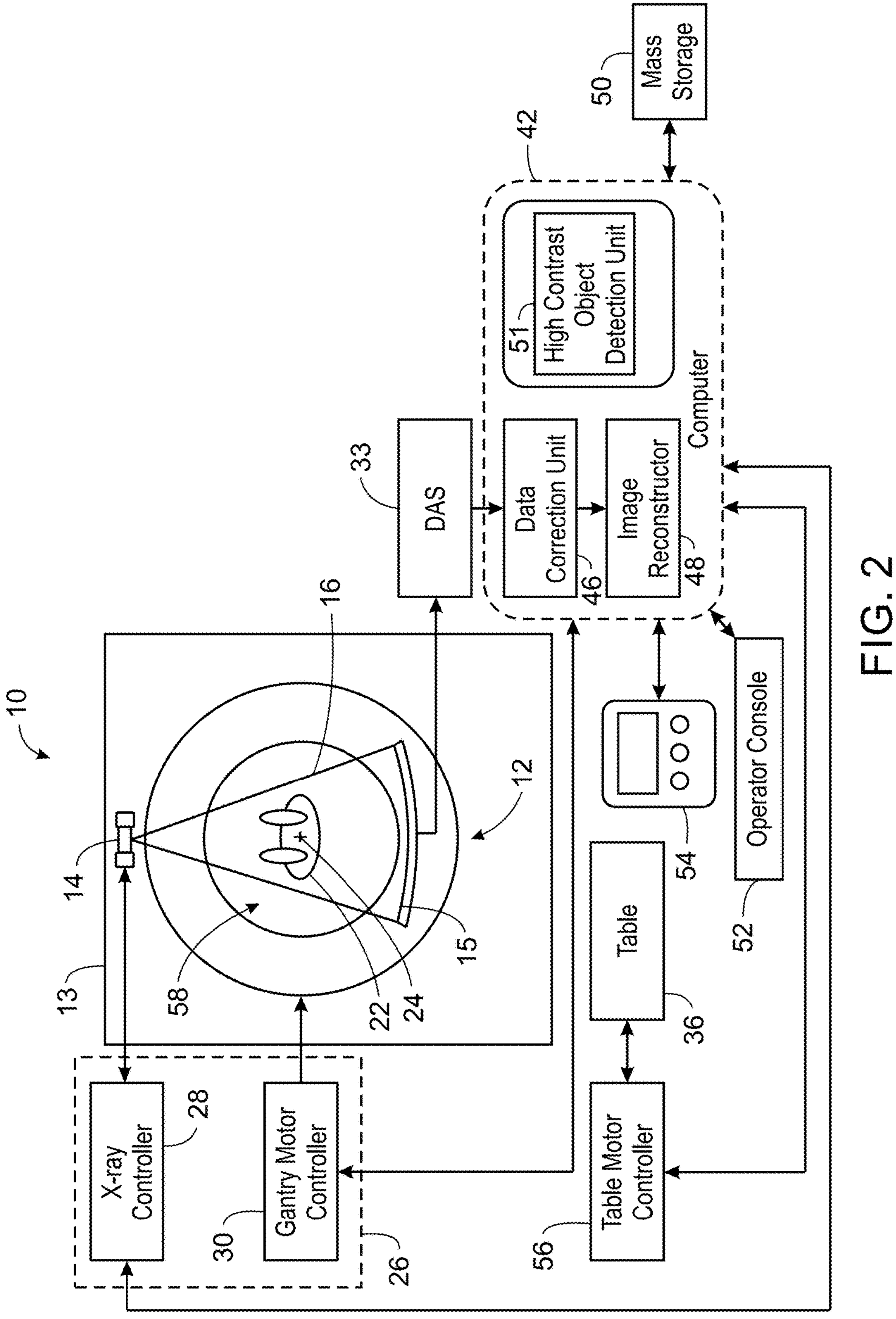
FIG. 2 is a block diagram of the CT imaging system in FIG. 1, in accordance with aspects of the present disclosure.

With the preceding in mind and referring to FIGS. 1 and 2, a CT imaging system 10 is shown, by way of example. The CT imaging system 10 of FIGS. 1 and 2 may be utilized with a dual-modality imaging system (e.g., positron emission tomography (PET)/CT imaging system). The CT imaging system 10 (e.g., CT scanner) includes a gantry 12 coupled having a housing 13 (e.g., gantry housing). The gantry 12 has a rotating component and a stationary component. The gantry 12 has an X-ray source 14 that projects a beam of X-rays 16 toward an X-ray detector assembly or X-ray detector array 15 (e.g., having a plurality of detector modules) on the opposite side of the gantry 12. The X-ray source 14 and the X-ray detector assembly 15 are disposed on the rotating portion of the gantry 12. The X-ray detector assembly 15 is coupled to data acquisition systems (DAS) 33. The plurality of detector modules of the X-ray detector assembly 15 detect the projected X-rays that pass through a patient or subject 22, and DAS 33 converts the data to digital signals for subsequent processing. Each detector module of the X-ray detector assembly 15 in a conventional system produces an analog electrical signal that represents the intensity of an incident X-ray beam and hence the attenuated beam as it passes through the patient 22. During a scan to acquire X-ray projection data, gantry 12 and the components mounted thereon rotate about a center of rotation 24 (e.g., isocenter) so as to collect attenuation data from a multitude of view angles relative to the imaged volume.

Rotation of gantry 12 and the operation of X-ray source 14 are governed by a control mechanism 26 of CT system 10. Control mechanism 26 includes an X-ray controller 28 that provides power and timing signals to the X-ray source 14 and a gantry motor controller 30 that controls the rotational speed and position of gantry 12.

A computer 42 (separate from or a part of the CT imaging system 10) includes a data correction unit 46 for processing or correcting the CT scan data from the DAS 33. The computer 42 also includes an image reconstructor 48. The image reconstructor 48 receives sampled and digitized X-ray data from DAS 33 and performs high-speed reconstruction. The reconstructed image is applied as an input to the computer 42, which stores the image in a mass storage device 50. The computer 42 further includes a high contrast object (high attenuating object) detection unit 51 that analyzes reconstructed images (derived from pre-scan workflow scans such as scout scans, calibration scans, or air scans taken before a diagnostic scan) from the image reconstructor 48 for the presence of a high contrast object or a high attenuating object. Computer 42 also receives commands and scanning parameters from an operator via console 52. An associated display 54 allows the operator to observe the reconstructed image and other data from the computer 42. For example, the associated display 54 may display an image (e.g., composite image) with areas of high attenuating objects highlighted, alerts, and/or recommendations associated with detected high attenuating objects. The operator supplied commands and parameters are used by computer 42 to provide control signals and information to the DAS 33, X-ray controller 28, and gantry motor controller 30. In addition, computer 42 operates a table motor controller 56, which controls a motorized table 36 to position the patient 22 relative to the gantry 12. Particularly, table 36 moves portions of the patient 22 through a gantry opening or bore 58.

The computer 42 include includes processing circuitry. The processing circuitry may be one or more general or application-specific microprocessors. The processing circuitry may be configured to execute instructions stored in a memory to perform various actions. For example, the processing circuitry may be utilized for generating images from pre-workflow scan data. The processing circuitry may also be utilized for analyzing reconstructed images (derived from pre-scan workflow scans such as scout scans, calibration scans, or air scans taken before a diagnostic scan) for the presence of a high contrast object or a high attenuating object and generating a composite image with the detected high contrast object or high attenuating object identified. The processing circuitry may further be utilized to provide alerts and/or recommendations related to the detection of the high contrast object or the high attenuating object.

Figure 3:
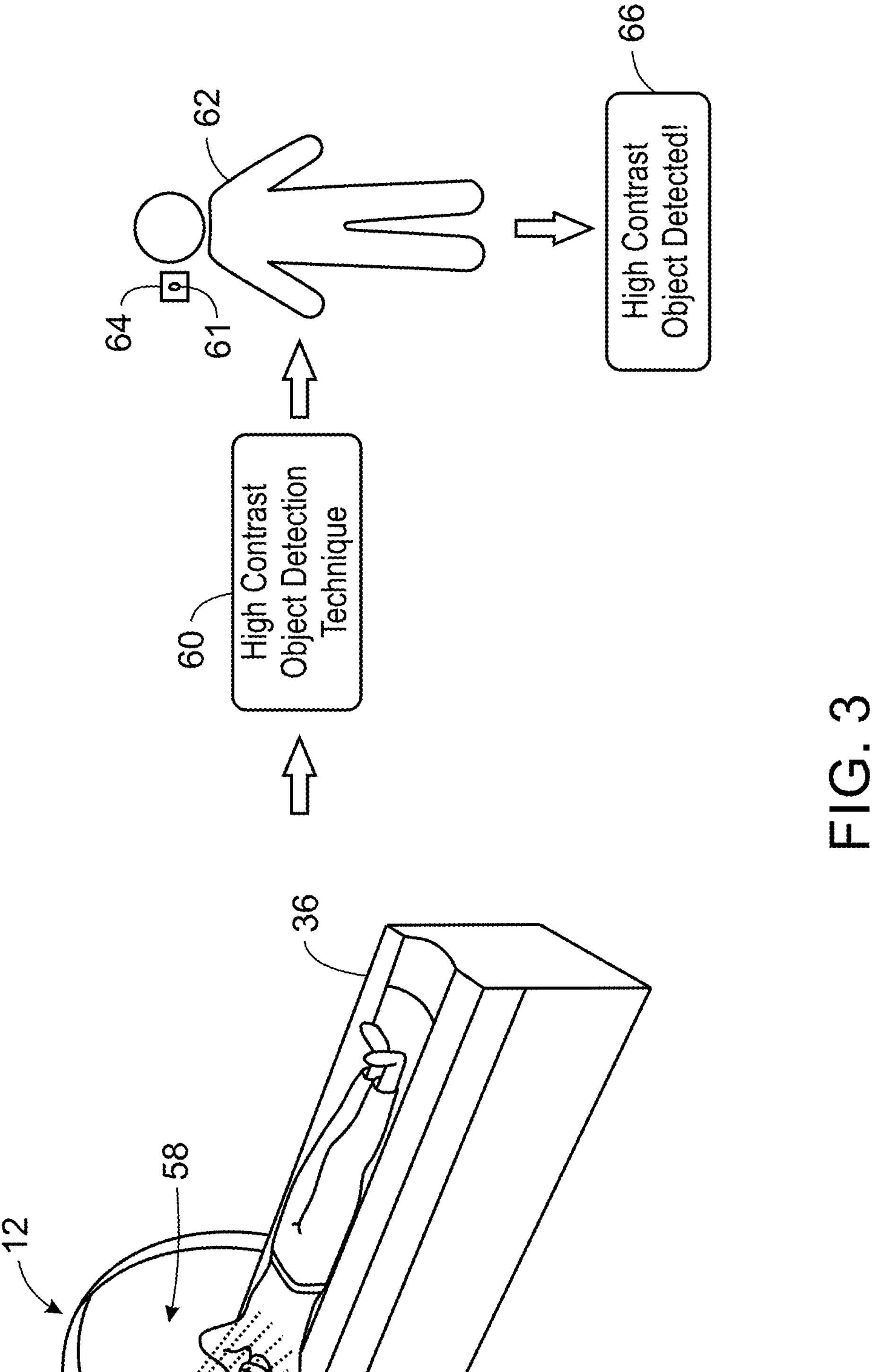
FIG. 3 is a schematic diagram of a workflow for detecting a high contrast object, in accordance with aspects of the present disclosure.

FIG. 3 is a schematic diagram of a workflow for detecting a high contrast object. FIG. 3 depicts the patient 22 undergoing a non-diagnostic scan (as part of the pre-scan (pre-diagnostic scan) workflow) utilizing the CT imaging system 10 (not all components of the CT imaging system 10 are shown). In particular, patient 22 is disposed within the bore 58 of the gantry 12 and a scout scan is performed. In certain embodiments, the scout scan is part of a calibration scan. A high contrast object detection feature (indicated by reference numeral 60) performs a high contrast object detection technique on a plurality of images generated from the scan data acquired during the scout scan to determine the presence of a high contrast object or a high attenuating object 61 is present in at least one of the images. If the presence of the high contrast object or the high attenuating object 61 is detected, an image 62 (e.g., composite image) may be displayed (e.g., on a display of an operator console of the CT imaging system 10). In the image 62, the high contrast object or the high attenuating object 61 is highlighted as indicated by the reference numeral 64. In certain embodiments, an alert (e.g., textual alert) may be provided as well (e.g., displayed on a display of the operator console of the CT imaging system 10), as indicated by reference numeral 66, indicating the detection of the high contrast object or the high attenuating object 61.

Figure 4:
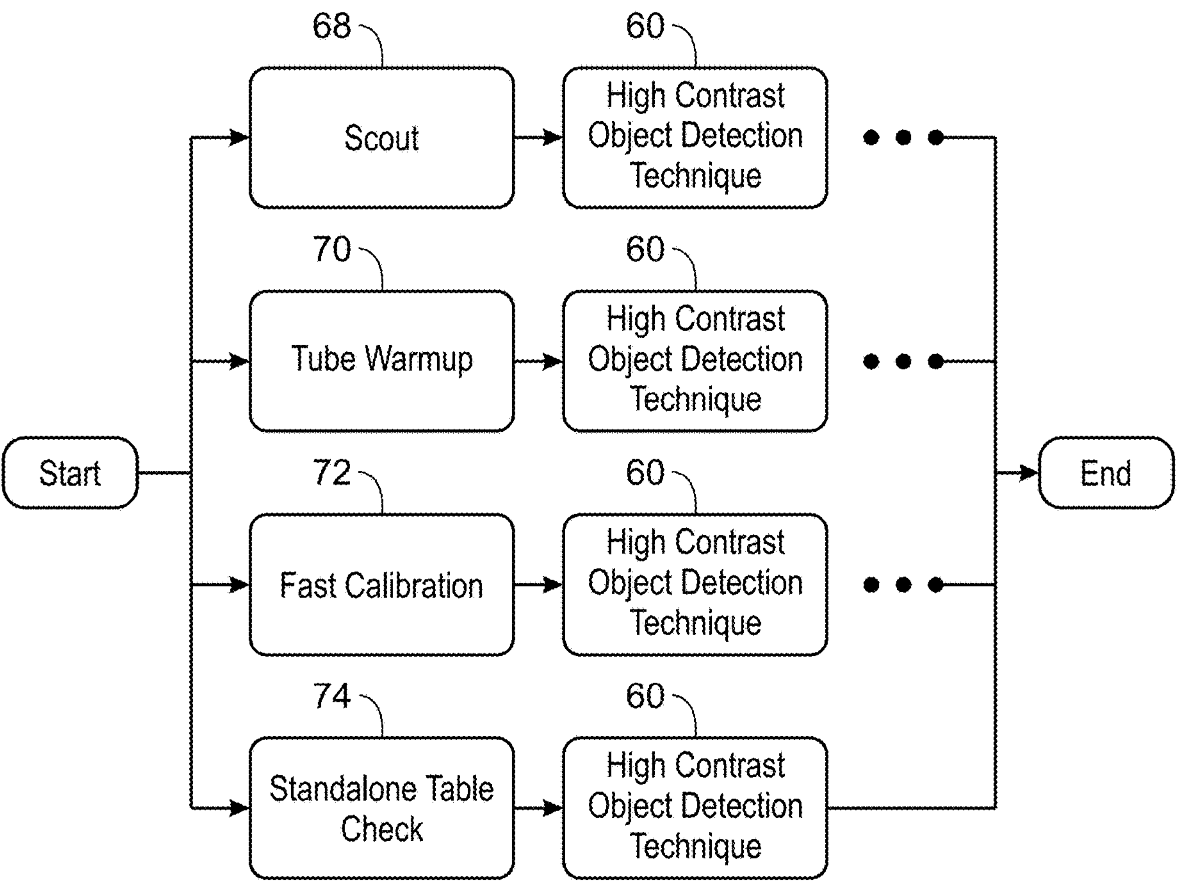
FIG. 4 is a schematic diagram of different workflows that a high contrast object detection feature can be utilized with, in accordance with aspects of the present disclosure.

The high contrast object detection feature (or technique) described herein may be utilized with a variety of different workflows utilizing a CT imaging system. FIG. 4 is a schematic diagram of different workflows that the high contrast object detection feature 60 can be utilized with. As depicted, the high contrast object detection feature 60 may be utilized as part of a pre-scan (e.g., pre-diagnostic scan) workflow such as a scout scan 68 to detect for the presence of a high contrast object or a high attenuating object present within the patient or outside the body of the patient (e.g., on the table or an accessory of the table). The scout scan 68 is utilized in setting the appropriate landmarks for a region of interest of a patient that will be undergoing a diagnostic scan. Thus, during the scout scan 68, the patient will be disposed within the bore of the gantry of the CT imaging scanner. In certain embodiments, the scout scan 68 may be part of a calibration scan prior to the diagnostic scan.

Also, as depicted, the high contrast object detection feature 60 may be utilized as part of a pre-scan (e.g., pre-diagnostic scan such as an air scan) workflow such as an X-ray tube warmup 70 to detect for the presence of a high contrast object or a high attenuating object present on the scan window of the CT detector, the table, or an accessory of the table. The X-ray tube warmup 70 is done without a subject within the bore of the gantry of the CT scanner. The X-ray tube warmup 70 is carried out prior to a scanning session or sessions where the X-ray tube has not been utilized in a while and cooled below a certain threshold.

Further, as depicted, the high contrast object detection feature 60 may be utilized as part of a pre-scan (e.g., pre-diagnostic scan such as an air scan) workflow such as a fast calibration scan 72 to detect for the presence of a high contrast object or a high attenuating object present on the scan window of the CT detector, the table, or an accessory of the table. The fast calibration scan 72 is done without a subject within the bore of the gantry of the CT scanner. The fast calibration scan 72 is carried out prior to a scanning session or sessions to detect the efficiency of the X-ray detector of the CT scanner.

Also, as depicted, the high contrast object detection feature 60 may be utilized as part of an independent scan (not part of a pre-scan workflow prior to a diagnostic scan) workflow such as standalone table check 74 to detect for the presence of a high contrast object or a high attenuating object present on the table or an accessory of the table of the CT imaging scanner. The standalone table check 74 is done without a subject (but with the table) within the bore of the gantry of the CT scanner. A similar standalone check may be utilized without the table within the bore of the gantry to detect for the presence of a high contrast object or a high attenuating object present of the scan window of the CT scanner.

Figure 5:
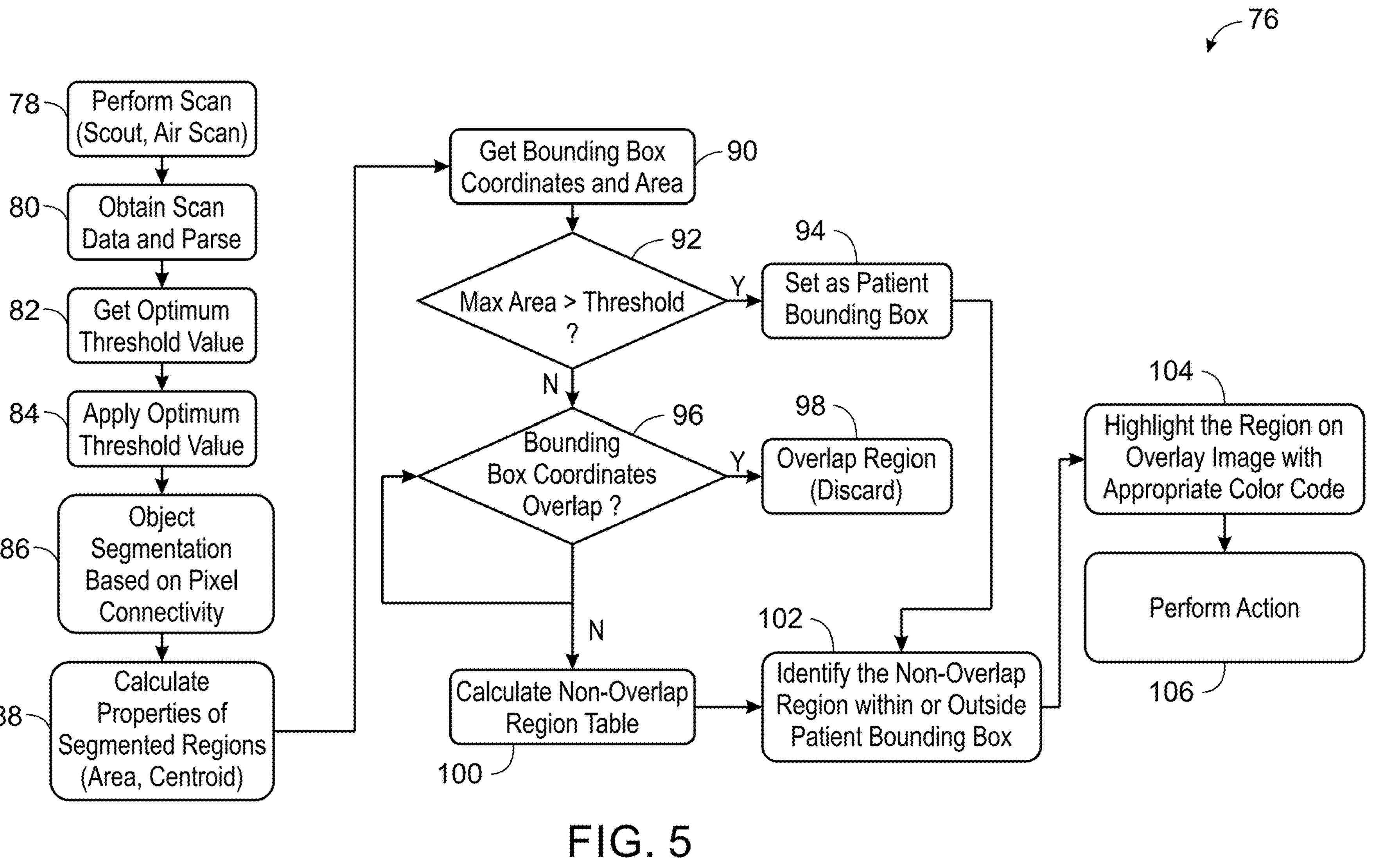
FIG. 5 is a flowchart of a method for identifying (or detecting) a high contrast object or a high attenuating object in medical imaging data, in accordance with aspects of the present disclosure.

FIG. 5 is a flowchart of a method 76 for identifying (or detecting) a high contrast object or a high attenuating object in medical imaging data. The method 76 may be performed by one or more components (e.g., processing circuitry) of the CT imaging system 10 in FIGS. 1 and 2. One or more steps of the method 76 may be performed simultaneously and/or in a different order than depicted in FIG. 5.

The method 76 includes performing a scan (e.g., non-diagnostic scan) utilizing a CT scanner of a CT system (e.g., CT system 10 in FIGS. 1 and 2) (block 78). In certain embodiments, the scan may be a scout scan. In certain embodiments, the scout scan may be part of a calibration scan. In certain embodiments, the scan may an air scan. In certain embodiments, the scan is a pre-scan (e.g., pre-diagnostic scan) as part of workflow performed prior to performing a diagnostic scan. In certain embodiments, the scan is an independent scan (e.g., as part of a standalone check) not associated with a workflow prior to performing a diagnostic scan. In certain embodiments (e.g., the scout scan), a subject or patient is disposed within the bore of a gantry of CT scanner during the scan. In certain embodiments (e.g., air scan), no subject or patient or phantom is disposed within the bore of the gantry of the CT scanner during the scan (i.e., in the imaging space between the X-ray source and the detector so that the detector array is irradiated by un-attenuated X-ray beam). Instead, only a table and/or accessories on the table are disposed within the bore of the gantry of the CT scanner during the scan. In certain embodiments (e.g., air scan for standalone check), event the table is not disposed within the bore of the gantry of the CT scanner during the scan.

The method 76 also includes obtaining the scan data from the non-diagnostic scan and parsing the scan data for each view (block 80). The method 76 further includes getting or calculating an optimum threshold value (i.e., to produce maximum difference in CT values in scan data) for generating an image for each view (block 82). The method 76 even further includes applying the optimum threshold value for generating an image for each view (block 84). The images converted from the scan data are binary images (e.g. grayscale images).

The method 76 still further includes performing (for each image) object segmentation based on pixel connectivity into individual objects (i.e., segmented regions) (block 86). The method 76 yet further includes characterizing (for each image) the individual objects by calculating properties (e.g., pixel connectivity properties) of the individual objects (i.e., segmented regions) (block 88). The pixel connectivity properties may include one or more of area, centroid, orientation, circularity, eccentricity, or other properties.

The segmented image regions are processes with a dynamic table that enable determining overlapping and non-overlapping identified regions. The method 76 includes getting or determining (for each image) bounding shape coordinates (e.g., bounding box coordinates) and area for each of the segmented regions (block 90). The method 76 also includes determining (for each image) for each bounding shape (e.g., bounding box) of each segmented region if its max area is greater than a threshold value (e.g., set area threshold value) (block 92). If the max area of a bounding shape is greater than the threshold value then the method 76 includes setting or designating the bounding shape as a patient or subject bounding shape (e.g., patient or subject bounding box) (block 94). For each image there is only one bounding shape set as the patient or subject bounding shape. In certain embodiments, for images (e.g., derived from air scans) that do not include a patient there may not be a patient or subject bounding shape. If the max area of a bounding shape is not greater than the threshold value then the method 76 includes determining if the coordinates of the bounding shape overlap with the bounding shape coordinates of one or more other bounding shapes (e.g., one or more other bounding boxes) (block 96). If the coordinates of the bounding shape overlap with the bounding shape coordinates of one or more other bounding shapes, the method 76 includes discarding the overlapping region (block 98). If the coordinates of the bounding shape do not overlap with the bounding shape coordinates of one or more other bounding shapes, the method 76 includes calculating a table (e.g., of parameters or coordinates) for the non-overlapping region (block 100). The non-overlapping region includes a high contrast object or a high attenuation object (e.g., due to a contrast agent spill or metal).

The method 76 further includes identifying (for any image where it applies) whether a non-overlapping region is located within or outside the subject or patient bounding shape (block 102). The method 76 still further includes highlighting the non-overlapping region by generating a composite image (e.g., for display on a display of an operator console of the CT scanner) with the patient bounding shape and a second bounding shape (e.g., second bounding box) for the non-overlapping region when present overlaid on the image, wherein each bounding shape overlaid on the image is color-coded to indicate a status of each bounding shape (block 104). In certain embodiments, there may be more than one non-overlapping region highlighted on the composite image. In certain embodiments, if there is not a non-overlapping region, only the patient bounding shape is shown on the composite image and it is color-coded a first color (e.g., green) to indicate the image is good (i.e., free of a high contrast object or a high attenuating object) and no further action is required related to any high contrast or high attenuating object. In certain embodiments, if there is a non-overlapping region, the patient bounding shape is color-coded as a second color (e.g., magenta) different from the first color to indicate the detection of the presence of a high contrast object or a high attenuation object. The bounding shape of the high contrast object or the high attenuation object may be color-coded a third color (e.g., red or blue) different from both the first color and the second color. In certain embodiments, the bounding shape of a high contrast object or a high attenuation object (e.g., metal) within the patient bounding shape may be color-coded a different color (e.g., blue) from the bounding shape of another high contrast object or high attenuation object (e.g., contrast from spill) located outside the patient bounding shape.

The method 76 also includes performing a further action (block 106). In certain embodiments, the action includes automatically activating a metal artifact reduction processing (if not already activated) if a bounding shape of a non-overlapping region is located within the patient bounding shape. In certain embodiments, the action includes causing an alert to be displayed (e.g., on a display of an operator console of the CT scanner) indicating the detection of the presence of the high contrast object or the high attenuation object. In certain embodiments, the action includes causing a recommendation (e.g., to clean a contrast spill) to be displayed (e.g., on a display of an operator console of the CT scanner). In certain embodiments, the actions may be non-gating (i.e., an action (e.g., cleaning) must occur before proceeding further) and stop the process (e.g., scanning, calibration, etc.) from continuing. In certain embodiments, the action may be gating (i.e., an action that will not stop the process (e.g., scanning, calibration, etc.) from continuing).

Figure 6:
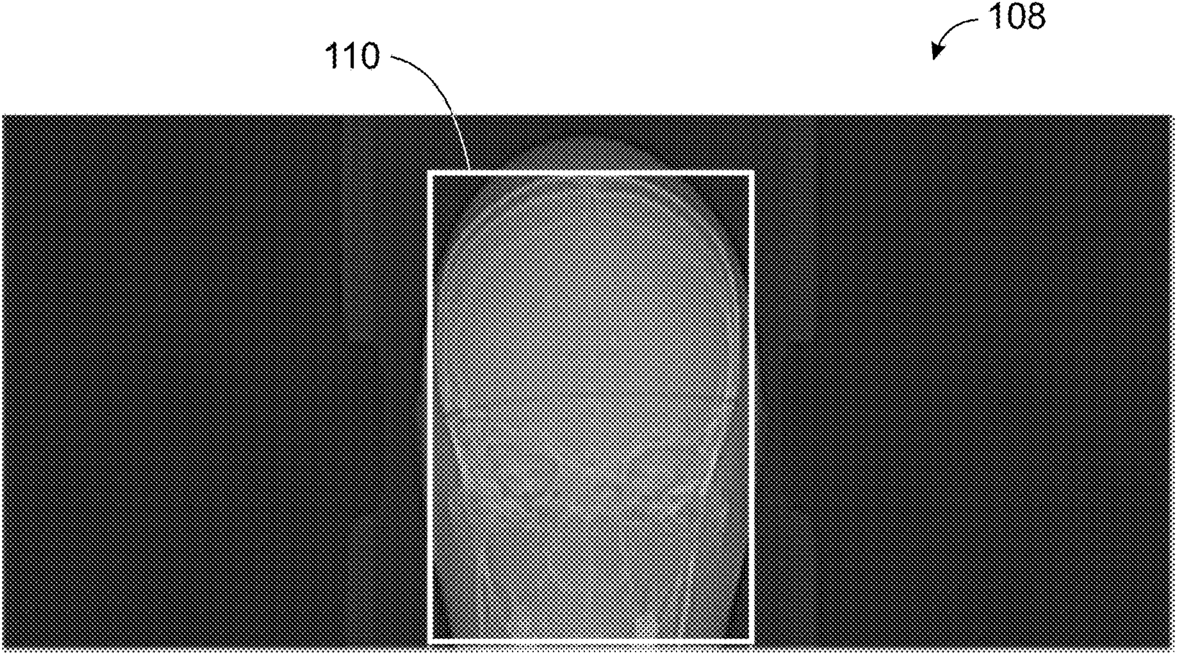
FIG. 6 is a composite image depicting a status of a scout image after utilization of a high contrast object detection feature (e.g., with no high contrast object or high attenuating object detected), in accordance with aspects of the present disclosure.

FIG. 6 is a composite image 108 depicting a status of a scout image after utilization of a high contrast object detection feature (e.g., with no high contrast object or high attenuating object detected) as described above. A scout image was generated from scan data acquired during a pre-scan workflow scan (e.g., a scout scan) with a subject within the bore of the gantry of the CT scanner as described in the method 76 in FIG. 5. In addition, the high contrast object detection feature was utilized on the scout scan to detect for the presence of a high contrast object or a high attenuating object as described in the method 76 in FIG. 5. No high contrast object or high attenuating object was detected in the scout scan. The composite image 108 was generated after the analysis utilizing the high contrast object detection feature. The composite image 108 includes a patient bounding box 110 overlaid on the scout image (e.g., grayscale image) bounding the portion of the patient scanned. The patient bounding box 110 is highlighted and color-coded. In certain embodiments, the patient bounding box 110 is encoded a color (e.g., green) to indicate the image is good (i.e., free of a high contrast object or a high attenuating object) and no further action is required related to any high contrast object. As depicted, the composite image 108 lacks any bounding boxes for an identified non-overlapping region having a high contrast object or a high attenuation object.

Figure 7:
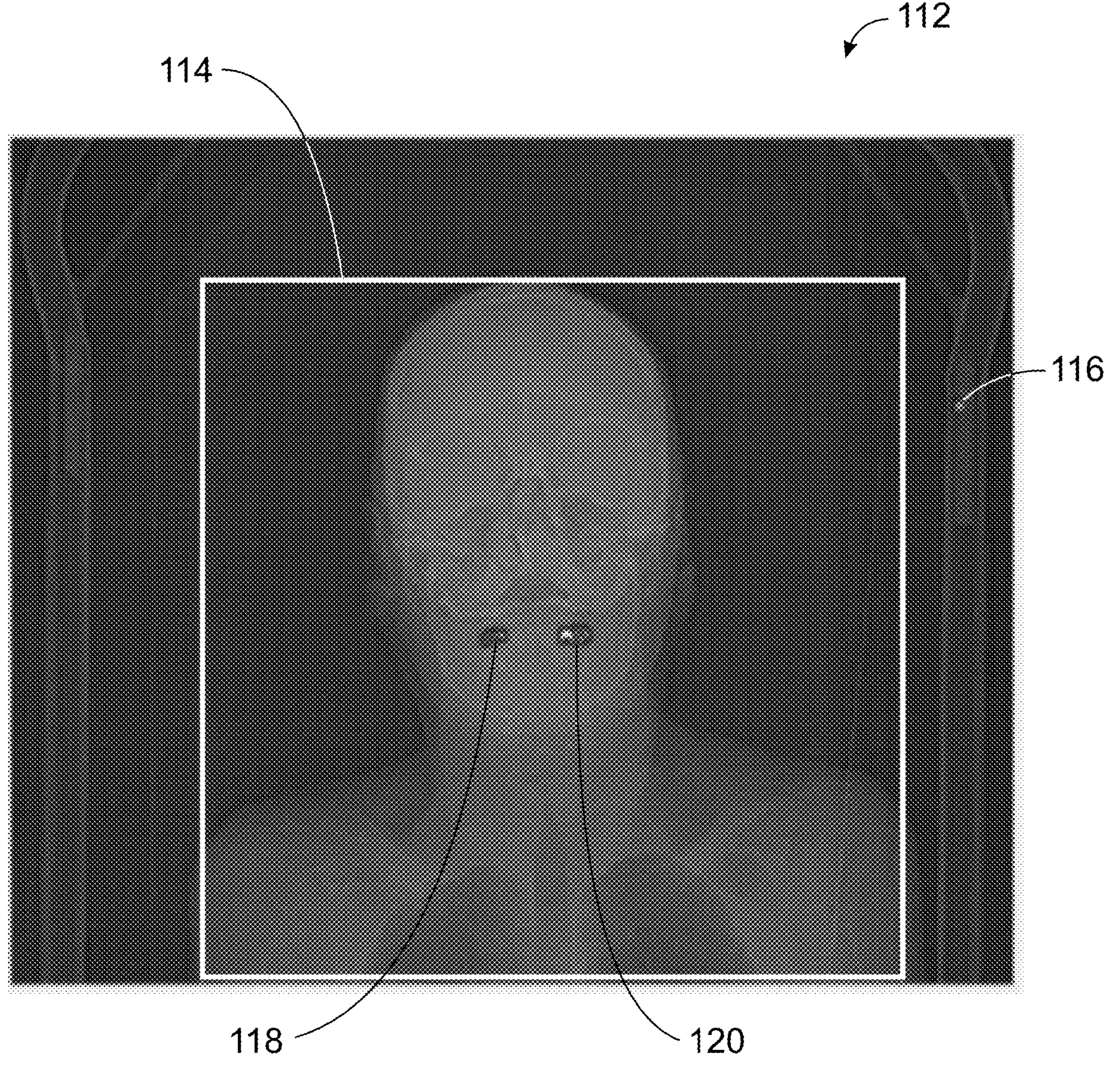
FIG. 7 is a composite image depicting a status of a scout image after utilization of a high contrast object detection feature (e.g., with multiple high contrast objects or high attenuating objects detected), in accordance with aspects of the present disclosure.

FIG. 7 is a composite image 112 depicting a status of a scout image after utilization of a high contrast object detection feature (e.g., with multiple high contrast objects or high attenuating objects detected) as described above. A scout image was generated from scan data acquired during a pre-scan workflow scan (e.g., a scout scan) with a subject within the bore of the gantry of the CT scanner as described in the method 76 in FIG. 5. In addition, the high contrast object detection feature was utilized on the scout scan to detect for the presence of a high contrast object or a high attenuating object as described in the method 76 in FIG. 5. Multiple high contrast objects or high attenuating objects were detected in the scout scan. The composite image 112 was generated after the analysis utilizing the high contrast object detection feature. The composite image 108 includes a patient bounding box 114 overlaid on the scout image (e.g., grayscale image) bounding the portion of the patient scanned. The patient bounding box 114 is highlighted and color-coded. In certain embodiments, the patient bounding box 114 is encoded a color (e.g., magenta) to indicate the presence of a detected high contrast object or high attenuating object (which is different from the color of the patient bounding box 110 in FIG. 6 where no high contrast object or high attenuating object was detected). As depicted, the composite image 108 also includes bounding boxes for identified non-overlapping regions having high contrast objects or high attenuation objects overlaid on the scout image. Bounding box 116 is disposed about a high contrast object (e.g., contrast spill) located outside of the patient bounding box 114. Bounding box 116 is highlighted and color-coded. In certain embodiments, the bounding box 116 is encoded a color (e.g., red) to indicate the presence of the detected high contrast object outside the patient bounding box 114. The color of the bounding box 116 is different from any color of the patient bounding box 114. Bounding boxes 118, 120 are disposed about a high attenuating object (e.g., metal within the patient) located within of the patient bounding box 114. Bounding boxes 118, 120 are each highlighted and color-coded. In certain embodiments, the bounding boxes 118, 120 are each encoded a color (e.g. blue) to indicate the presence of the detected high contrast object within the patient bounding box 114. The color of the bounding boxes 118, 120 are different from any color of the patient bounding box 114 and the color any bounding box (e.g., bounding box 116) located outside the patient bounding box 114.

Figure 8:
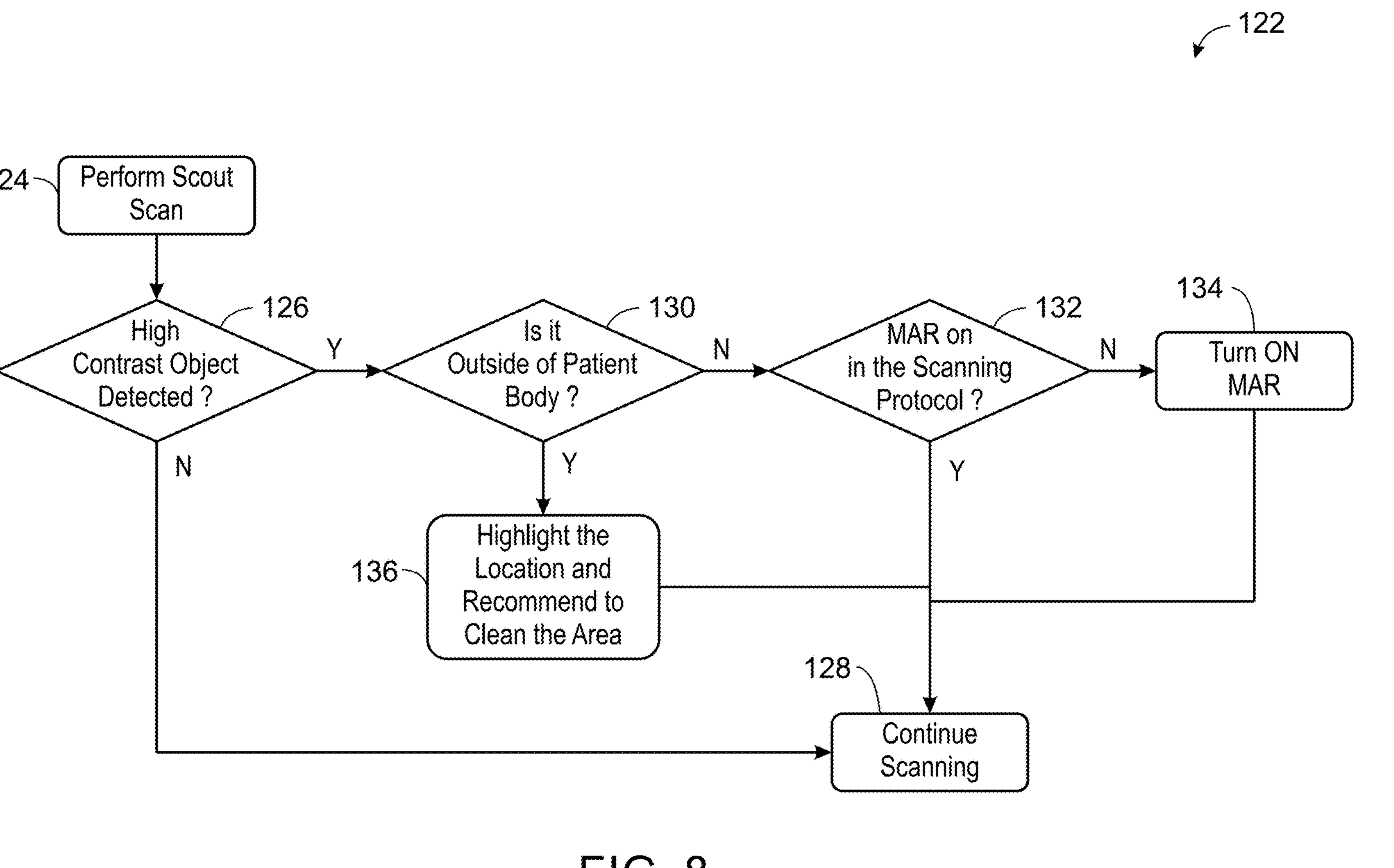
FIG. 8 is a flowchart of a method for identifying (or detecting) a high contrast object or a high attenuating object in medical imaging data, in accordance with aspects of the present disclosure.

FIG. 8 is a flowchart of a method 122 for identifying (or detecting) a high contrast object or a high attenuating object in medical imaging data. The method 122 may be performed by one or more components (e.g., processing circuitry) of the CT imaging system 10 in FIGS. 1 and 2. One or more steps of the method 122 may be performed simultaneously and/or in a different order than depicted in FIG. 8.

The method 122 includes performing a scout scan (e.g., non-diagnostic scan) utilizing a CT scanner of a CT system (e.g., CT system 10 in FIGS. 1 and 2) (block 124). In certain embodiments, the scout scan may be part of a calibration scan. The scout can is a pre-scan (e.g., pre-diagnostic scan) as part of workflow performed prior to performing a diagnostic scan. A subject or patient is disposed within the bore of a gantry of CT scanner during the scout scan. From this scout scan, an image (e.g., scout image) is generated as described above in the method 76 in FIG. 5. A scout image may be determined for each respective view. The actions depicted in the method 122 may be non-gating (i.e., operator/technologist can choose to continue scan).

The method 122 also includes determining (for multiple scout images) whether a high contrast object or a high attenuating object is present within the scout scan (block 126). In certain embodiments, this determination may be made as described above in the method 76 in FIG. 5. In particular, the scout scan may be segmented utilizing pixel connectivity and the segmented regions may be characterized utilizing pixel connectivity properties. In addition, bounding shapes (e.g., bounding boxes) may be utilized to determine a patient bounding shape (e.g., patient bounding box) and bounding shapes (e.g., bounding boxes) for identified non-overlapping regions (e.g., having a high contrast object or a high attenuation object).

If a high contrast object or a high attenuation object is not detected, the method 122 includes continuing with the scanning (e.g., pre-scan workflow scan and/or subsequent diagnostic scan) (block 128). If a high contrast object or a high attenuation object is detected, the method 122 further includes determining (for each scout image having a high contrast object or a high attenuation object) whether the high contrast object or the high attenuation object is outside the body of the patient (block 130). In certain embodiments, this determination may be based on whether a bounding box for a high object or the high attenuation object is located outside of the patient bounding box.

If the high contrast object or the high attenuation object is not located outside of the patient body (i.e., the high contrast object or the high attenuation object is located within the patient body), the method 122 includes determining if metal artifact reduction (MAR) processing is activated (e.g., turned on) in the scanning protocol (block 132). If metal artifact reduction processing is already turned on, the method 122 includes continuing with the scanning (e.g., pre-scan workflow scan and/or subsequent diagnostic scan) (block 128). In certain embodiments, the bounding box for the detected high contrast object or the high attenuation object may be highlighted and color-coded as an overlay on a scout image as part of a displayed composite image as shown in FIG. 7. If metal artifact reduction processing is not activated, the method 122 includes automatically activating (e.g., turning on) metal artifact reduction processing (block 134) and then continuing with the scanning (e.g., pre-scan workflow scan and/or subsequent diagnostic scan) (block 128).

If the high contrast object or the high attenuation object is located outside of the patient body, the method 122 includes highlighting the location of the high contrast object or the high attenuation object and providing a recommendation to clean the area where the high contrast object or the high attenuation object is located (block 136). As part of highlighting the location of the high contrast object or the high attenuation object, a composite image of color-encoded bounding boxes for the patient and the high contrast object or the high attenuation object overlaid on the scout image may be generated and displayed (e.g., on a display of an operator console of the CT scanner). In addition, a recommendation may be displayed on the display of the operator console of the CT scanner. In certain embodiments, an additional recommendation may be provided (e.g., to stop the scan or start the process over after cleaning). In certain embodiments, an alert (e.g., text stating a high contrast object or a high attenuation object was detected) may be displayed on the display on the operator console of the CT scanner. After highlighting the location of the high contrast object or the high attenuation object and providing a recommendation to clean the area, the method 122 includes continuing with the scanning (e.g., pre-scan workflow scan and/or subsequent diagnostic scan) (block 128).

Figure 9:
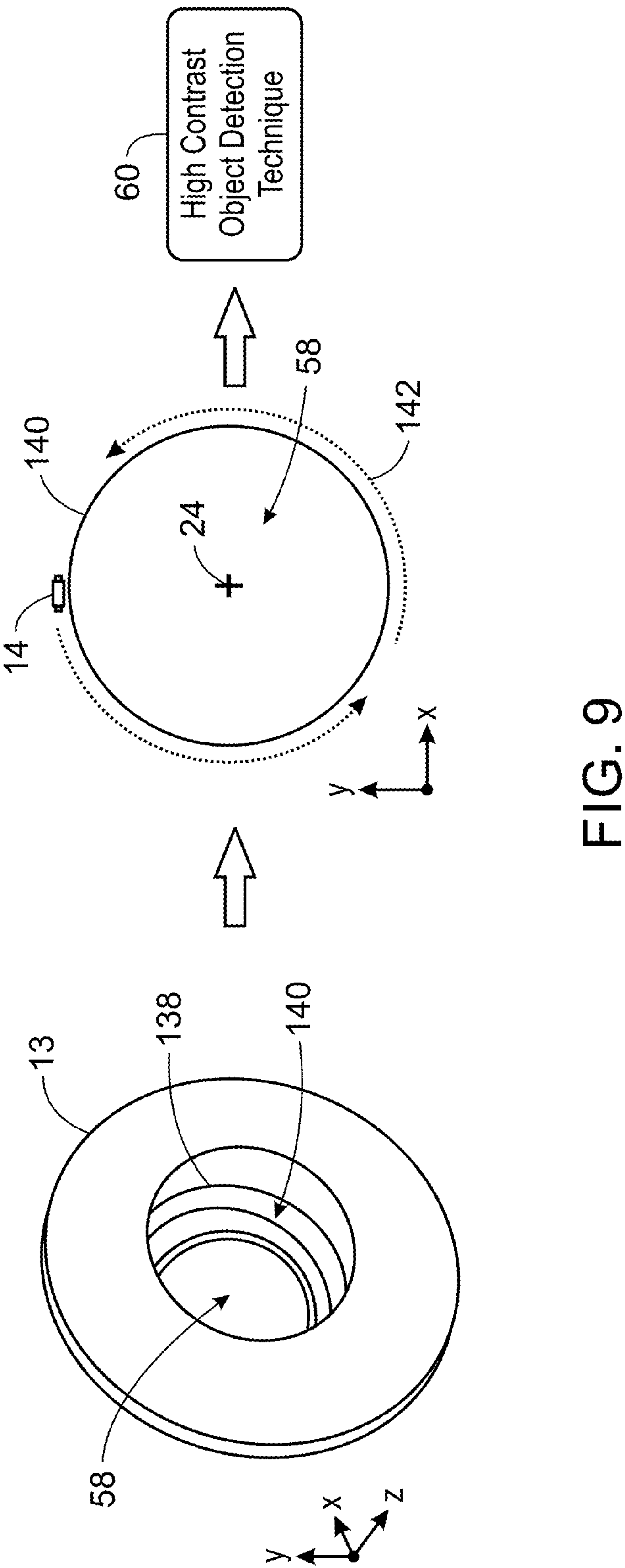
FIG. 9 is a schematic diagram of a workflow for detecting a high contrast object or a high attenuating object in a scan window, in accordance with aspects of the present disclosure.

FIG. 9 is a schematic diagram of a workflow for detecting a high contrast object or a high attenuating object in a scan window 138. The left side of FIG. 9 depicts the gantry 12 of a CT scanner (e.g., of the CT imaging system 10 in FIGS. 1 and 2). The gantry 12 includes a gantry cover 137 configured to be located on a front portion of the gantry housing adjacent the CT table. The gantry includes an annular scan window 138 disposed within an interior wall 140 of the gantry 12 formed within the opening or the bore 58 of the gantry 12. The scan window 138 is made of an X-ray transparent material that enables X-rays emitted from an X-ray source to pass through an object or subject being imaged for detection by a detector. The scan window 138 is constructed so as to be fitted between components of the housing of the gantry 12 (e.g., front and back covers) to fill a gap. During an imaging session, a subject or patient is moved within the bore 58. The scan window 138 self-supports and acts as a safety barrier to keep the subject or patient from contacting rotating components within the gantry 12.

In certain embodiments, whether part of a pre-scan workflow or as a standalone check, the scan window 138 may be inspected utilizing the high contrast object detection technique or feature 60 as described above. As depicted in the middle of FIG. 6, an air scan is conducted where the X-ray source 14 does a complete rotation (e.g., 360 degrees as indicated by arrows 142) in a circumferential direction relative to the axis of rotation 24 without a subject or patient (and in some cases table) located within the bore. Analysis of the air scan data as described above utilizing the high contrast object detection technique 60 determines any high contrast object or high attenuation object is present on the scan window 138.

Figure 10:
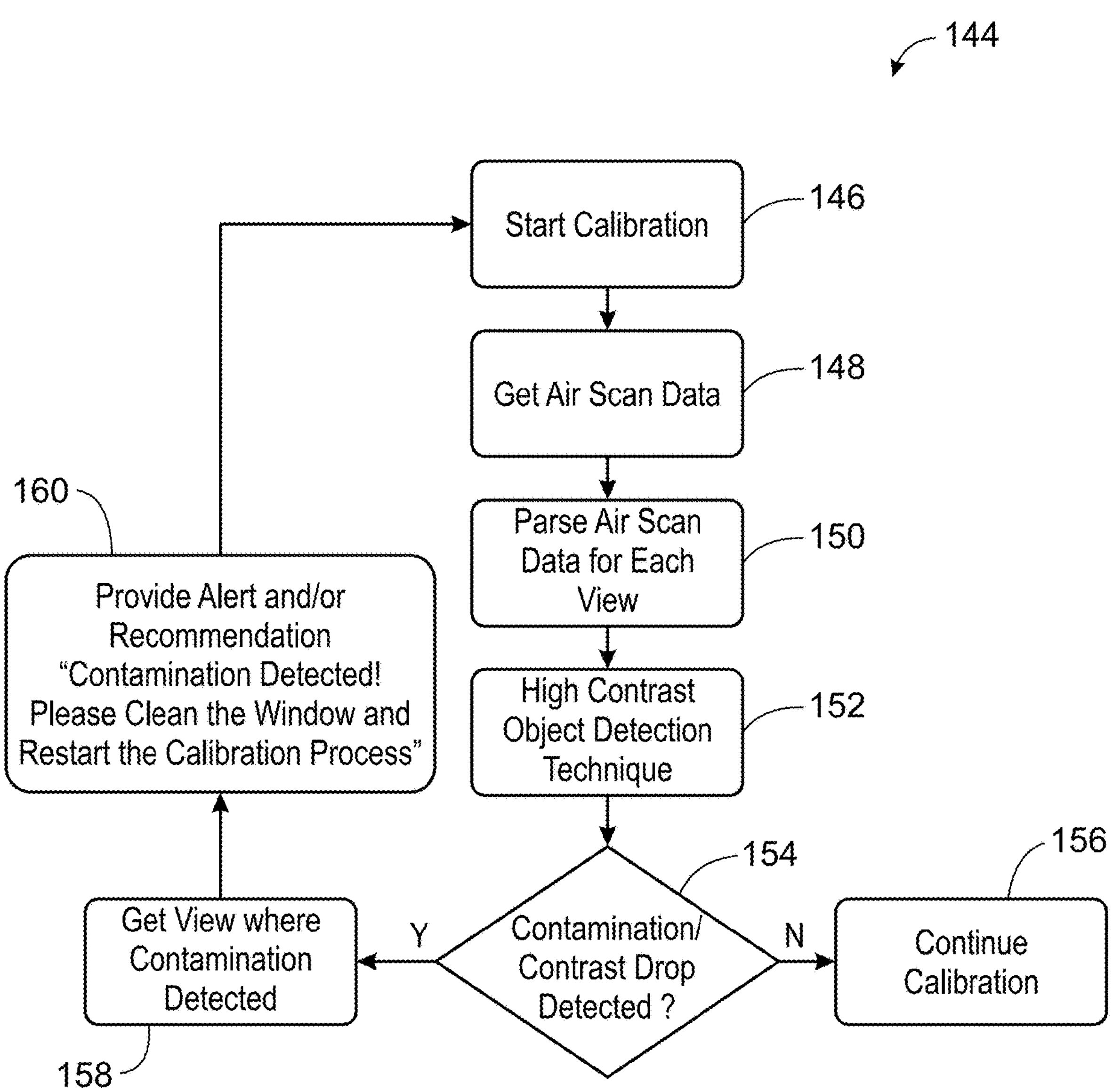
FIG. 10 is a flowchart of a method for identifying (or detecting) a high contrast object or a high attenuating object on a scan window of a CT scanner, in accordance with aspects of the present disclosure.
Figure 11:
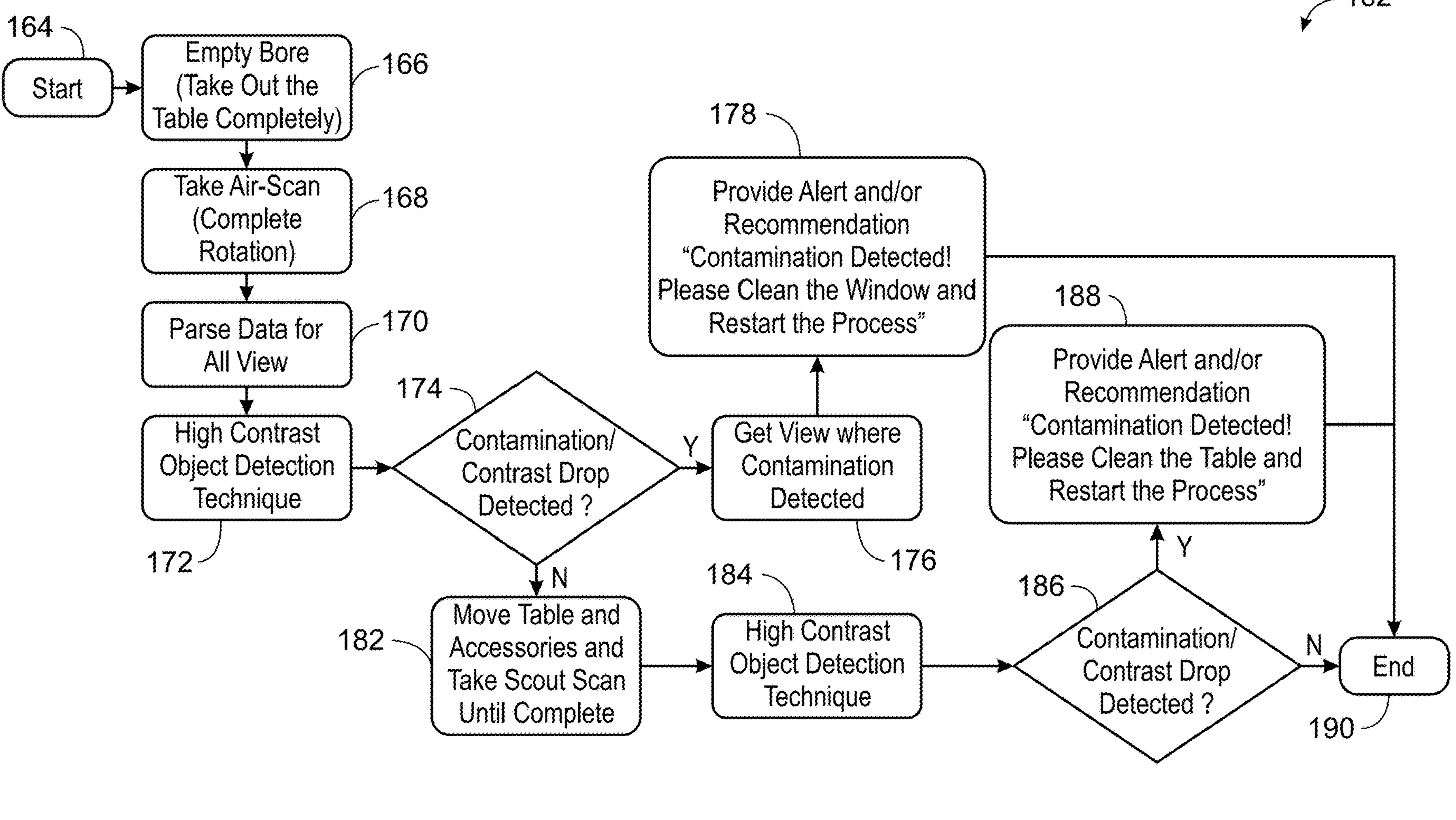
FIG. 11 is a flowchart of a method for identifying (or detecting) a high contrast object or a high attenuating object on a component of a CT scanner (e.g., scan window, table, and/or accessories), in accordance with aspects of the present disclosure.

FIGS. 10 and 11 are examples of methods that may be utilized using a workflow similar to that depicted in FIG. 9 to identify or detect a high contrast object or a high attenuating object on a component of a CT scanner. FIG. 10 is a flowchart of a method 144 for identifying (or detecting) a high contrast object or a high attenuating object on a scan window of a CT scanner. The method 144 may be performed by one or more components (e.g., processing circuitry) of the CT imaging system 10 in FIGS. 1 and 2. One or more steps of the method 144 may be performed simultaneously and/or in a different order than depicted in FIG. 10.

The method 144 includes starting a calibration scan (block 146). In certain embodiments, the calibration scan may be a fast calibration as described in FIG. 4. The calibration is an air scan without the subject (e.g., patient) or table disposed within a bore of the CT scanner. The method 144 also includes getting or obtaining air scan data from the air scan (block 148). The method 144 further includes parsing the air scan data for each view (block 150). From this air scan, an image is generated as described above in the method 76 in FIG. 5. An image may be generated for each respective view.

The method 144 also includes applying (for each image) the high contrast object detection technique as described above (block 152). The method 144 further includes determining (for each image) whether high contrast object or high attenuating object contamination is detected within the image (and, thus, on the scan window of the CT scanner) (block 154). In certain embodiments, this determination may be made as described above in the method 76 in FIG. 5. In particular, each image derived from the air scan may be segmented utilizing pixel connectivity and the segmented regions may be characterized utilizing pixel connectivity properties. In addition, bounding boxes may be utilized to determine bounding boxes for identified non-overlapping regions (e.g., having a high contrast object or a high attenuation object).

If high contrast object or high attenuation object contamination is not detected, the method 144 includes continuing with the calibration (block 156). If high contrast object or high attenuation object contamination is detected, the method 144 further includes getting or obtaining the view (i.e., image) where the high contrast object or the high attenuation object contamination is detected (block 158). In certain embodiments, contamination may be detected in multiple views (or images). The method 144 even further includes providing an alert and/or recommendation in response to detecting high contrast object or high attenuation object contamination (block 160). The alert and/or recommendation may be displayed on an operator console of the CT scanner in the form of a popup message. The alert may indicate that contamination was detected on the scan window. The recommendation may indicate that the scan window needs to be cleaned and the calibration process needs to be restarted. Upon the cleaning the window, the method 144 includes restarting the calibration (block 146).

FIG. 11 is a flowchart of a method 162 for identifying (or detecting) a high contrast object or a high attenuating object on a component of a CT scanner (e.g., scan window, table, and/or accessories). The method 162 may be performed by one or more components (e.g., processing circuitry) of the CT imaging system 10 in FIGS. 1 and 2. One or more steps of the method 162 may be performed simultaneously and/or in a different order than depicted in FIG. 11.

The method 162 includes starting a standalone check (e.g., dedicated spill detection mode) (block 164). The method 162 also includes emptying the bore of the gantry of the CT scanner (i.e., taking out the table completely) (block 166). The method 162 further includes starting an air scan (block 168). The air scan is conducted where the X-ray source does a complete rotation (e.g., 360 degrees as shown in FIG. 9) in a circumferential direction relative to the axis of rotation. The method 162 also includes getting or obtaining air scan data from the air scan and parsing the air scan data for each view (block 170). From this air scan, an image is generated as described above in the method 76 in FIG. 5. An image may be generated for each respective view.

The method 162 also includes applying (for each image) the high contrast object detection technique as described above (block 172). The method 162 further includes determining (for each image) whether high contrast object or high attenuating object contamination is detected within the image (and, thus, on the scan window of the CT scanner) (block 174). In certain embodiments, this determination may be made as described above in the method 76 in FIG. 5. In particular, each image derived from the air scan may be segmented utilizing pixel connectivity and the segmented regions may be characterized utilizing pixel connectivity properties. In addition, bounding boxes may be utilized to determine bounding boxes for identified non-overlapping regions (e.g., having a high contrast object or a high attenuation object).

If high contrast object or high attenuation object contamination is detected on the scan window, the method 162 further includes getting or obtaining the view (i.e., image) where the high contrast object or the high attenuation object contamination is detected (block 176). In certain embodiments, contamination may be detected in multiple views (or images). The method 162 even further includes providing an alert and/or recommendation in response to detecting high contrast object or high attenuation object contamination (block 178). The alert and/or recommendation may be displayed on an operator console of the CT scanner in the form of a popup message. The alert may indicate that contamination was detected on the scan window. The recommendation may indicate that the scan window needs to be cleaned and the standalone check needs to be restarted. Following this, the method 162 includes ending the standalone check (block 180).

If high contrast object or high attenuation object contamination is not detected on the scan window, the method 162 includes moving the table (without any patient) and any accessories (i.e., any additional component (e.g., head holder) that can be attached to the table and undergo scanning) into the bore of the CT scanner and starting a scout scan (block 182). The scout scan data is obtained from the scout scan and parsed for each view. From this scout scan, a scout image is generated as described above in the method 76 in FIG. 5. A scout image may be generated for each respective view.

The method 162 also includes applying (for each scout image) the high contrast object detection technique as described above (block 184). The method 162 further includes determining (for each scout image) whether high contrast object or high attenuating object contamination is detected within the scout image (and, thus, on the table and/or accessories) (block 186). In certain embodiments, this determination may be made as described above in the method 76 in FIG. 5. In particular, each scout image derived from the scout scan may be segmented utilizing pixel connectivity and the segmented regions may be characterized utilizing pixel connectivity properties. In addition, bounding boxes may be utilized to determine bounding boxes for identified non-overlapping regions (e.g., having a high contrast object or a high attenuation object).

If high contrast object or high attenuation object contamination is not detected on the table and/or accessories, the method 162 includes ending the standalone check (block 180). If high contrast object or high attenuation object contamination is not detected on the table and/or accessories, the method 162 includes providing an alert and/or recommendation in response to detecting high contrast object or high attenuation object contamination on the table and/or accessories (block 186). The alert and/or recommendation may be displayed on an operator console of the CT scanner in the form of a popup message. The alert may indicate that contamination was detected on the table and/or accessories. The recommendation may indicate that the table and/or accessories need to be cleaned and the standalone check needs to be restarted. Following this, the method 162 includes ending the standalone check (block 180).

Technical effects of the disclosed embodiments include providing systems and methods for an intelligent scout scan (or calibration scan) technique to identify high contrast object (or high attenuating object) in a computed tomography (CT) scanner. The disclosed techniques provide a safety check feature to ensure CT data acquisition is free from any unintended high attenuating object in the scan field of view (SFOV) and improve clinical workflow robustness. In addition, the disclosed techniques provide a holistic approach combining system hardware along with software for computation and analysis to improve the efficiency and robustness of the workflow by detecting and identifying high attenuation objects that may produce artifacts in the reconstructed images and alerting an operator to follow appropriate procedures.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A computer-implemented method for identifying a high contrast or highly attenuating object in medical imaging data, comprising:

- generating an image from scan data acquired during a non-diagnostic scan utilizing a computed tomography (CT) scanner;
- performing object segmentation based on pixel connectivity on the image to generate segmented regions;
- calculating pixel connectivity properties of the segmented regions, wherein the pixel connectivity properties comprise one or more of area, centroid, orientation, circularity, and eccentricity;
- obtaining respective bounding shape coordinates and area for bounding shapes of the segmented regions;
- designating a first bounding shape of the bounding shapes as a subject bounding shape for a subject scanned during the non-diagnostic scan;

identifying a non-overlapping region from the segmented regions having the high contrast or highly attenuating object when present;

determining whether the non-overlapping region when present is within or outside the subject bounding shape; and generating a composite image with the subject bounding shape and a second bounding shape for the non-overlapping region when present overlaid on the image, wherein each bounding shape overlaid on the image is color-coded to indicate a status of each bounding shape, wherein the subject bounding shape is color-coded a first color to indicate that the image does not contain any high contrast or highly attenuating object and no further action is required related to any high contrast or highly attenuating object, and wherein the subject bounding shape is color coded a second color different from the first color to indicate the presence of the high contrast or highly attenuating object.

2. The computer-implemented method of claim 1, wherein the second bounding shape is color-coded a third color different from both the first color and the second color to indicate a presence of the high contrast or highly attenuating object outside the subject bounding shape.

3. The computer-implemented method of claim 2, further comprising causing display of a recommendation on a display to remove the high contrast or highly attenuating object.

4. The computer-implemented method of claim 1, wherein the second bounding shape is color-coded a third color different from both the first color and the second color to indicate a presence of the high contrast or highly attenuating object within the subject.

5. The computer-implemented method of claim 4, further comprising automatically turning on or add metal artifact reduction processing when the high contrast or highly attenuating object is present within the subject.

6. The computer-implemented method of claim 1, wherein the non-diagnostic scan is a scout scan.

* * * * *